United States Patent
Boyer et al.

(10) Patent No.: US 7,488,861 B2
(45) Date of Patent: Feb. 10, 2009

(54) PROCESS FOR THE CO-PRODUCTION OF CUMENE AND SECONDARY BUTYL BENZENE

(75) Inventors: Christopher C. Boyer, Pasadena, TX (US); Mitchell E. Loescher, Pasadena, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 549 days.

(21) Appl. No.: 11/082,263

(22) Filed: Mar. 17, 2005

(65) Prior Publication Data

US 2006/0211901 A1 Sep. 21, 2006

(51) Int. Cl.
*C07C 2/66* (2006.01)

(52) U.S. Cl. .................. 585/467; 585/475; 585/323; 203/DIG. 6

(58) Field of Classification Search .......... 585/467, 585/475, 323; 203/DIG. 6
See application file for complete search history.

(56) References Cited

U.S. PATENT DOCUMENTS

| 4,316,997 A | 2/1982 | Vaughan |
| 4,371,714 A | 2/1983 | Young |
| 4,423,254 A | 12/1983 | Olah |
| 4,469,908 A | 9/1984 | Burress |
| 5,055,627 A | 10/1991 | Smith, Jr. et al. |
| 5,176,883 A | 1/1993 | Smith, Jr. et al. |
| 5,210,348 A | 5/1993 | Hseih et al. |
| 5,243,115 A | 9/1993 | Smith, Jr. et al. |

FOREIGN PATENT DOCUMENTS

| EP | 0 439 632 A1 * | 7/1991 |
| EP | 0 719 750 A1 | 7/1996 |
| JP | 404218591 A * | 8/1992 |

OTHER PUBLICATIONS

Notification of Transmittal of the International Search Report and The Written Opinion of the International Searching Authority, or the Declaration, PCT/US05/46628; mailed Sep. 24, 2007 (8 pages).

* cited by examiner

*Primary Examiner*—Thuan Dinh Dang
(74) *Attorney, Agent, or Firm*—Osha Liang LLP

(57) ABSTRACT

Cumene and secondary butyl benzene are produced simultaneously in a distillation column reactor by feeding propylene, butylene and benzene to the reactor. Unreacted benzene is removed as overheads and cumene and secondary butyl benzene are removed as products. The catalysts used are acid cation exchange resins, zeolites, particularly beta zeolite.

7 Claims, 1 Drawing Sheet

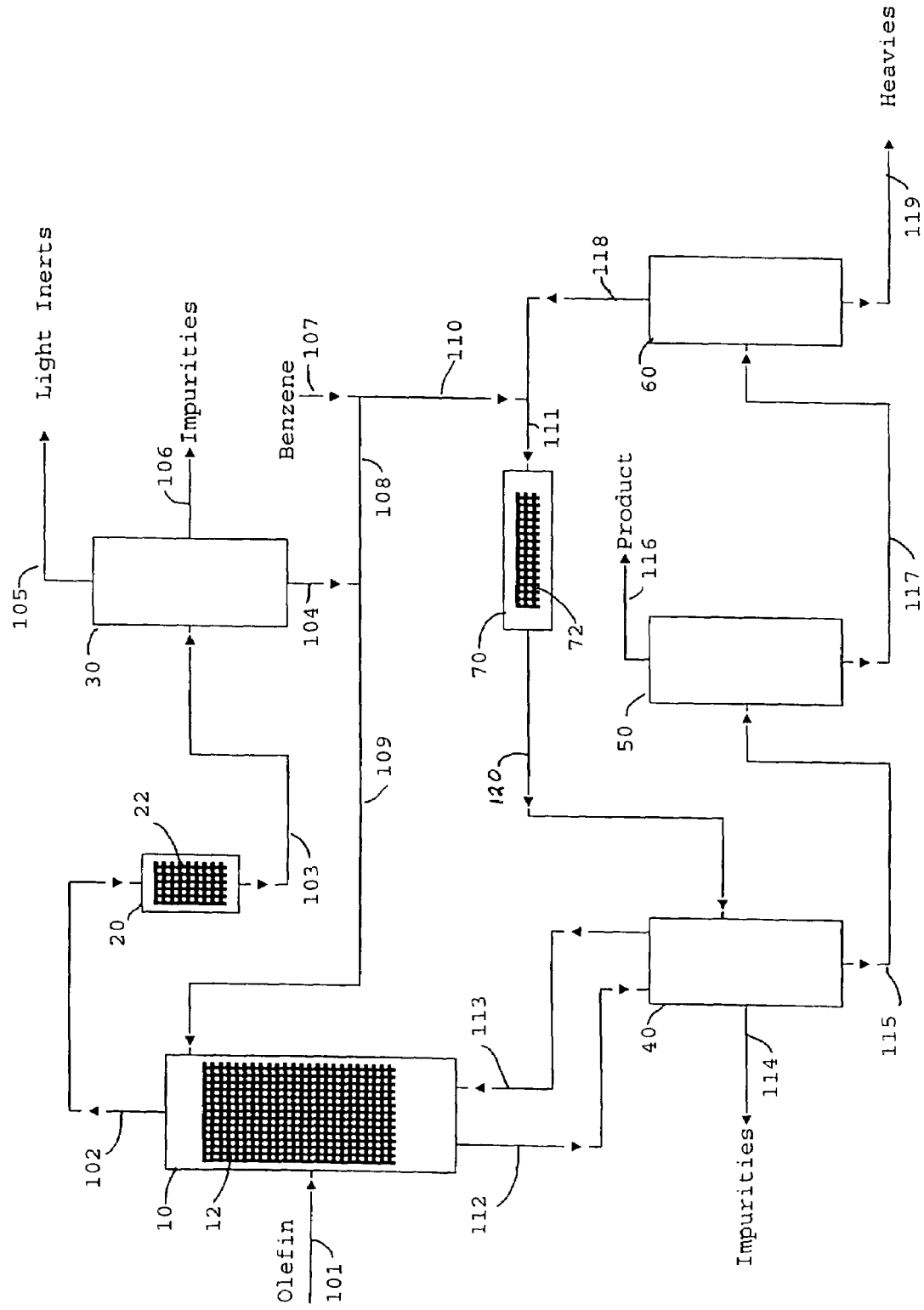

PROCESS FOR THE CO-PRODUCTION OF CUMENE AND SECONDARY BUTYL BENZENE

BACKGROUND OF THE INVENTION

1. Field of the Invention

The present invention relates to a process for the alkylation of organic aromatic compounds. More particularly the invention relates to a process for the co-production of cumene and secondary butyl benzene by concurrently alkylating benzene with propylene and butylene. More particularly the invention relates to a process for the concurrent co-production of cumene and secondary butyl benzene in a distillation column reactor where the unreacted benzene and olefin are concurrently separated from the products by fractional distillation.

2. Related Art

Cumene and secondary butyl benzene (SBB) are currently produced by the reaction of benzene and the respective olefin, i.e., propylene or butylene by acid catalysis. In some known processes the catalyst is highly corrosive and has a relatively short life, e.g., $AlCl_3$, $H_3PO_4$ on clay, $BF_3$ on alumina, and others require periodic regeneration, e.g., molecular sieves. The exothermicity of the reaction and the tendency to produce polysubstituted benzene require low benzene conversions per pass with large volume recycle in conventional processes.

U.S. Pat. Nos. 4,371,714 and 4,469,908 disclose straight pass alkylation of aromatic compounds using molecular sieve catalysts in fixed beds, however, both references disclose coking of the catalyst as a problem which necessitates frequently shutting down the unit and regeneration of the catalyst. U.S. Pat. Nos. 4,316,997 and 4,423,254 both disclose the use of acidic resins in fixed beds for the alkylation of aromatic compounds. Coking is also a problem with these catalysts.

U.S. Pat. No. 5,243,115 discloses a process for the alkylation of benzene with a $C_2$ to $C_{20}$ olefin in a distillation column reactor containing a fixed bed acidic catalyst in the form of a distillation structure.

SUMMARY OF THE INVENTION

Briefly, the present invention is a process for the co-production of cumene and secondary butyl benzene by the alkylation of benzene comprising contacting the benzene with and a stream containing propylene and butylene in the presence of an acidic catalyst. The reaction may be carried out preferably in a catalytic distillation in which the process for the concurrent production of cumene and secondary butyl benzene comprises:

(a) concurrently:
  (i) reacting benzene with propylene and butylene under conditions of temperature and pressure in the presence of an aromatic alkylation catalyst to form a reaction mixture containing unreacted benzene, unreacted propylene, unreacted butylene, cumene and secondary butyl benzene;
  (ii) separating the unreacted benzene, unreacted propylene and unreacted butylene from the cumene and secondary butyl benzene by fractional distillation;
(b) recovering the unreacted benzene, unreacted propylene and unreacted butylene as overheads; and
(c) recovering cumene and secondary butyl benzene as bottoms.

Suitable acidic catalysts include zeolites such as molecular sieves (mole sieves) and cation exchange resins. More specifically the mole sieve or cation exchange resin catalyst is prepared in a manner so as to allow fluid flow through the bed for catalytic contact as described in U.S. Pat. Nos. 4,215,011; 4,302,356 and 4,443,559 which are incorporated herein in their entirety.

For the purposes of the present invention, the term "catalytic distillation" includes reactive distillation and any other process of concurrent reaction and fractional distillation in a column, i.e., a distillation column reactor, regardless of the designation applied thereto.

BRIEF DESCRIPTION OF THE DRAWING

The FIGURE is a schematic representation of a preferred embodiment of one species of the present invention.

DETAILED DESCRIPTION OF THE INVENTION

The olefin, i.e, the propylene and butylene, are fed to the distillation column reactor at a point below the distillation reaction zone. The organic aromatic compound feed may be added at any point in the reactor, however, preferably it is added at the top of the distillation reaction zone as reflux. Also, in order to achieve high selectivity toward monosubstitution (which is a preferred aspect of the present invention), there is a large excess of the organic aromatic compound to the olefin in the reactor in the range of 2 to 100 moles of organic aromatic compounds per mole of olefin, that is, the net molar feed ratio of aromatic organic compound olefin may be close to 1:1, although the system is operated so as to maintain a substantial molar excess of organic aromatic compound to olefin in the reaction zone. Surprisingly, it has been found that under the preferred operating conditions of catalytic distillation for the alkylation of benzene, the kinetic rate for $C_4$ alkylation is of the same order of magnitude as the $C_3$ alkylation, the $C_4$ alkylation being only slightly faster and that the selectivity for the monoalkylate is the same on a molar basis for the $C_3$ and $C_4$ alkylations. It is believed that these properties are the result of the catalytic distillation mode of operation and allows the present concurrent production of cumene and secondary butyl benzene.

The alkylated product is the highest boiling material and is separated in the lower portion of the column usually as bottoms. The organic aromatic compounds are the second highest boiling components (excluding inerts) as noted above, however, by operating with a large excess of the organic aromatic compound, the major portion of the olefin is reacted; thereby reducing the separation and recovery problems. The operation of reactive distillation lies in an understanding of the principles associated with distillation. First, because the reaction is occurring concurrently with distillation, the initial reaction product is removed from the reaction zone as quickly as it is formed. The removal of the alkylation product minimizes polysubstitution, decomposition of the alkylation product and/or oligomerization of the olefin. Second, because the organic aromatic compound is boiling, the temperature of the reaction is controlled by the boiling point of that component at the system pressure. The heat of the reaction simply creates more boil up, but no increase in temperature. Third, the reaction has an increased driving force because the reaction products have been removed and cannot contribute to a reverse reaction (Le Chatelier's Principle).

As a result, a great deal of control over the rate of reaction and distribution of products can be achieved by regulating the system pressure. Also, adjusting the through-put (residence time and liquid hourly space velocity) gives further control of product distribution and degree of olefin conversion. The temperature in the reactor is determined by the boiling point of the liquid mixture present at any given pressure. The temperature in the lower portions of the column will reflect the constitution of the material in that part of the column, which will be higher than the overhead; that is, at constant pressure a change in the temperature of the system indicates a change in the reactant/product composition in the column. To change the temperature the pressure is changed. Temperature control in the reaction zone is thus controlled by the pressure; by increasing the pressure, the temperature in the system is increased, and vice versa. It can also be appreciated that in reactive distillation as in any distillation there is both a liquid phase (internal reflux) and a vapor phase. Thus, the reactants are partially in liquid phase which allows for a more dense concentration of molecules for reaction, whereas, the concurrent fractionation separates product and unreacted materials, providing the benefits of a liquid phase system (and a vapor phase system) while avoiding the detriment of having all of the components of the reaction system continually in contact with the catalyst which would limit the conversion to the equilibrium of the reaction system components.

The present alkylation reaction can be carried out at sub- through super atmospheric pressure, e.g., 0.20 to 40 atmospheres. The temperature will vary depending on the reactants and product. Furthermore, the temperature along the column will be as in any distillation column, the highest temperature will be in the bottom and the temperature along the column will be the boiling point of the compositions at that point in the column under the particular conditions of pressure. Moreover, the exothermic heat of reaction does not change the temperature in the column, but merely causes more boil up. However, the temperatures within the column with the above considerations in mind will generally be in the range of 50° C. to 500° C., preferably 70° C. to 500° C. for the mole sieve and 70° C. to 200° C. for the cation exchange resin, and more preferably in the range of about 80° C. to 300° C. at pressures of 0.5 to 20 atmospheres for the mole sieve, and about 80° C. to 150° C. at 0.25 to 15 atmospheres for the resin catalyst.

A preferred method of operation of the reactive distillation is a liquid-continuous distillation column as described in U.S. patent application Ser. No. 10/357,123, filed Feb. 3, 2003, published Jan. 1, 2004, as US-2004-0000474-A1, which is incorporated herein its entirety. It has been found that vapor velocities greater than 50% of jet flood to less than 100% of jet flood will promote fractionation in bubble columns. Preferably, if the vapor velocities are pushed above about 70% of jet flood then the distillation performance of a given column packing becomes similar for both liquid continuous operation (bubble column mode) and vapor continuous operation (ordinary distillation tower mode).

The same tower can be operated either as a bubble column or as a distillation tower simply by controlling the liquid level above the packing or below it (usually in the reboiler for a distillation column) so that the packing is either in a liquid continuous mode or a vapor continuous one. The "flood point" (100% of jet flood) is defined as the point where vapor velocities are so great that reflux cannot return to the reboiler fast enough to maintain reboiler level. Above this point, the reboiler will run dry and no steady state operation can be maintained. A flow map may be used to define the jet flood point over a range of reflux ratios. The column packing or other internals (including trays or heat exchanger bundles) will not significantly alter the performance improvements disclosed here that result from operating at a high vapor rate expressed as a % of jet flood.

In carrying out the liquid continuous reactive distillation there will usually be three phases, although the solid phase is not required to carry out the liquid filled column distillation at over 50% of jet flood, in most applications there will be a solid phase. Simple distillation structures, such as rings, ball, polylobes, saddles or fibrous type structures, trays bubble, sieve etc.), or other distillation structures as known in the art, including the catalytic distillation structures of the type described in U.S. Pat. Nos. 5,266,546, 5,431,890, 5,073,236, 5,431,890 and 5,730,843.

In conducting liquid continuous distillation, the liquid may be merely materials to be separated by fractional distillation, or there may be added at the upper end of the column a liquid which is higher boiling, and which is intended to extract one or more components from the vapor in the column and exits as a bottoms. The liquid and vapor in the column may be reactive and the reaction product and feed may be separated more efficiently by the present distillation than by the mere stripping action of the gas at less than 50% of jet flood.

The olefins herein are contained in a stream which consists substantially of isobutylene and propylene or separate streams of each olefin. In the reactions according to the present invention, the olefin is a lower boiling material than the organic aromatic compound. In such instances any unreacted olefin will appear in the overheads product and may be recycled with any unreacted benzene. However, operating the reaction with far less than a stoichiometric amount of olefin in the reaction zone, as described, will normally keep the olefin level in the overheads low or entirely eliminated.

The organic aromatic compound in this case is benzene. The mole ratio of benzene to olefin in the reaction zone may be in the range of 2 to 100:1, preferably 2 to 50:1 and more desirably about 2 to 10:1. The greater the excess of organic aromatic compound the more the selectivity to the monosubstituted product is improved. Alkylation is forced to completion, since the simultaneous and concurrent fractionation and removal of the alkylation product from the distillation column reactor does not allow the products to contribute to the reverse reaction (Le Chatelier's Principle). However, very large molar excesses of organic aromatic compounds require a very high reflux ratio, and a low unit productivity. Hence, the correct ratio of organic aromatic compound to olefin must be determined for each combination of reactants as well as the acceptable olefin content in the overheads (as described above). In this particular embodiment which is of current commercial importance, isobutylene and propylene are reacted with benzene according to the present invention to form secondary butyl benzene and cumene, respectively. In both of these reactions the olefin is the most volatile component and it is desirable to react it rather than have some carried off overhead.

Naturally occurring zeolites have irregular pore size and are not generally considered as equivalent to synthetic zeolites. Many natural zeolites such as ferrierite feature a one-dimensional pore structure. In the present invention, however, naturally occurring zeolites are acceptable so long as they are substantially pure. Molecular sieves are porous crystalline, three-dimensional alumina-silicates of the zeolite mineral group. The term molecular sieve can be applied to both naturally occurring zeolites and synthetic zeolites. The balance of the present discussion shall be directed to the synthetic zeolites with the understanding that natural zeolites are considered equivalent thereto as indicated above, i.e., in so far as the natural zeolites are the functional equivalents to the synthetic zeolites.

Usually synthetic zeolites are prepared in the sodium form, that is, with a sodium cation in close proximity to each aluminum tetrahedron and balancing its charge. Some types of molecular sieves are, A, X, Y, L, erionite, omega, beta, and mordenite. The A type zeolites have relatively small pore size.

By the term pore size is meant the effective pore size (diameter) rather than the free pore size (diameter). Types X and Y have larger pore size (approximately 10 Å) and differ as to the range of ratio of $Al_2O_3$ to $SiO_2$ as:

Type X—$Al_2O_3$/2.0-3.0 $SiO_2$

Type Y—$Al_2O_3$/3.0-6.0 $SiO_2$

Type L and the other types listed have still higher ratios of $SiO_2$ to $Al_2O_3$ The mole sieve catalysts employed in the present invention are the acid form mole sieves or exhibit acidic characteristics. The acid form of the mole sieves is commercially available, but also may be prepared by treating the mole sieves with acid to exchange Na for hydrogen. Another method to produce the acid form is to treat the mole sieve with decomposable cations (generally ammonium ions) to replace Na with the decomposable ions and thereafter to heat the mole sieve to decompose the cation leaving the acid form. Generally the Na form mole sieve is treated with ammonium hydroxide nitrate to remove the Na and thereafter the mole sieve is heated to a temperature of about 350° C. to remove the ammonia. The removal of $Na^+$ ions with $NH^+_4$ is more easily carried out than with multivalent ions as described below and these catalysts are generally more active, but less stable to heat than the multivalent cation exchange forms. Mole sieves, which have had their alkali metal reduced to low levels by partial treatment with $NH^+_4$ and partial multivalent metal cation exchange, possess increased activity and increased stability. In addition to mole sieves which are acidic according to the Bronsted Theory, those mole sieves which exhibit acidic characteristics under the Lewis Theory, for example, calcium exchanged mole sieves are suitable for the present reaction. By exchanging the univalent cations (e.g.) $Na^+$) with multivalent cation, strong ionic activity is imparted. The ratio of $SiO_2$:$Al_2O_3$, valence and radius of the cation and the extent of exchange all affect the catalyst activity. In general activity increases with (1) increased $SiO_2Al_2O_3$ ratio, (2) decreased cation radius and an increase in cation valence. The effect of replacing univalent ions (e.g. $Na^+$) with bivalent (e.g. $Ca^{++}$) is much greater than replacing the bivalent ions with cations of greater valence.

The various types of mole sieves having reduced alkali metal content are characterized as the acid form molecular sieves and are all contemplated as useful in the present invention.

It would appear that the pore size within the crystal lattice may affect the selectivity. According to one theory of molecular sieve catalytic activity, zeolite catalysis occurs primarily inside the uniform crystal cavities, consequently zeolitic catalyst activity depends on the number of aluminum atoms in the crystal and thus on the chemical composition of the crystal. Moreover, these catalytic sites are fixed within the rigid structure of the crystal, so that access to site can be altered by altering the structure of the crystal. Suitable zeolites include Beta zeolite is preferred catalyst for the present process. Beta zeolite is a known synthetic crystalline alumino-silicate originally described in U.S. Pat. No. 3,308,069 which is hereby incorporated by reference for details of this zeolite, its properties and preparation. In particular, beta zeolite is identified by its characteristic X-ray diffraction pattern which is set out in Table 4 of the above referenced U.S. Pat. No. 3,308,069 This pattern, in terms of significant d values (Angstroms, radiation:K alpha doublet of copper, Geiger counter spectrometer), is reproduced in Table I below.

TABLE I

| d Values of Reflection in Beta Zeolite |
| --- |
| 11.4 ± 0.2 |
| 7.4 ± 0.2 |
| 6.7 ± 0.2 |
| 4.25 ± 0.1 |
| 3.97 ± 0.1 |
| 3.0 ± 0.1 |
| 2.3 ± 0.1 |

In U.S. Pat. No. 3,308,069 the beta zeolite is described in its as-synthesized forms as follows:

[$X$Na(1.0±0.1$X$)TEA]$AlO_2$. $Y$$SiO_2$. $W$$H_2O$ wherein X is less than 1, preferably less than 0.75, TEA represents tetraethylammonium ion, Y is greater than 5 and less than 100, and W is up to about 4, depending on the condition of dehydration and on the metal cation present, The patent also teaches that the sodium may be replaced by another metal ion using ion exchange techniques.

Subsequent publications such as European Patent Applications Nos. 95,304; 159,846; 159,847 and 164,939 have broadened the definition of beta zeolite to include materials prepared using templating agents other than tetraethylammonium hydroxide and materials having Si/Al atomic ratios greater than 100. Also, the zeolites described in European Patent Application Nos. 55,046 ("Nu 2") and 64,328 and British Patent Application No. 2,024,790 ("Boralite B") have structures and X-ray diffraction patterns very similar to that of beta zeolite and are included within the scope of the term "beta zeolite" as used herein.

The forms of beta zeolite which are most useful in the present invention are crystalline aluminosilicates having the empirical formula:

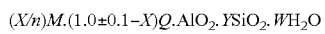

($X/n$)$M$.(1.0±0.1–$X$)$Q$.$AlO_2$. $Y$$SiO_2$. $W$$H_2O$ wherein X is less than 1, preferably less than 0.75, Y is greater than 5 and less than 100, W is up to about 4, M is a metal ion, n is the valence of M, and Q is a hydrogen ion, an ammonium ion or an organic cation, or a mixture thereof. Y is preferably greater than 5 and less than about 50. Thus the silicon to aluminum atomic ratio in the above formula is greater than 5:1 and less than 100:1, and preferably greater than 5:1 and less than about 50:1. M is typically a sodium ion from the original synthesis but may also be a metal ion added by ion exchange techniques. Suitable metal ions include those from Groups IA, IIA, IIIA of the Periodic Table or a transition metal. Examples of such ions include ions of lithium, potassium, calcium, magnesium, barium, lanthanum, cerium, nickel, palladium, and the like. It is also contemplated that other elements, such as gallium, boron and iron, can be substituted for aluminum in the above formula. Similarly, elements such as germanium and phosphorous can be variably substituted for silicon.

Suitable organic cations are those cations which are derived in aqueous solution from tetraethylammonium bromide or hydroxide, dibenzyl-1,4-diazabicyclo[2.2.2]octane chloride, dimethyldibenzyl ammonium chloride, 1,4-(1-azonium bicyclo[2.2.2]octane)butane dibromide or dihydroxide, and the like. These organic cations are known in the art and are described, for example, in European Patent Application Nos. 159,846 and 159,847, and U.S. Pat. No. 4,508,837. The preferred organic cation is the tetraethylammonium ion.

For high catalytic activity, the beta zeolite should be predominantly in its hydrogen ion form. Generally, the zeolite is converted to its hydrogen form by ammonium exchange followed by calcination. If the zeolite is synthesized with a high enough ratio of organonitrogen cation to sodium ion, calcination alone may be sufficient. It is preferred that, after calcination, a major portion of the cation sites are occupied by hydrogen ions and/or rare earth ions. It is especially preferred that at least 80% of the cation sites are occupied by hydrogen ions and/or rare earth ions.

Suitable acid cation exchange resins include those which contain sulfonic acid groups, and which may be obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethyl benzene, methyl styrene, vinyl chlorobenzene and vinyl xylene. A large variety of methods may be used for preparing these polymers; for example, polymerization alone or in admixture with other monovinyl compounds, or by crosslinking with polyvinyl compounds; for example, with divinyl benzene, divinyl toluene, divinylphenylether and others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric and chlorosulfonic acid, or by copolymerizing aromatic compounds which contain sulfonic acid groups (see e.g., U.S. Pat. No. 2,366,007). Further sulfonic acid groups may be introduced into the polymer which already contains sulfonic acid groups; for example, by treatment with fuming sulfuric acid, i.e., sulfuric acid which contains sulfur trioxide. The treatment with fuming sulfuric acid is preferably carried out at 0 to 150° C. and the sulfuric acid should contain sufficient sulfur trioxide so that it still contains 10 to 50% free sulfur trioxide after the reaction. The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent Specification 908,240). The ion exchange resin is generally used in a granular size of about 0.25 to 1 mm, although particles from 0.15 mm up to about 2 mm may be employed. The finer catalysts provide high surface area, but could also result in high pressure drops through the reactor requiring higher vapor velocities to agitate the catalyst. The macro reticular form of these catalysts have much larger surface area exposed and limited swelling which all of these resins undergo in a non-aqueous hydrocarbon medium compared to the gelular catalysts.

In their normal forms both the molecular sieves and the cation exchange resins are unsuitable for packing in a distillation column, and must then be prepared in the form of a catalytic distillation structure. The catalytic distillation structure must be able to function as catalyst and as mass transfer medium. The catalyst must be suitably supported and spaced within the column to act as a catalytic distillation structure, as disclosed in U.S. Pat. No. 5,266,546, where the catalyst is contained in a woven wire mesh structure, which is hereby incorporated by reference. Other catalytic distillation structures useful for this purpose are disclosed in U.S. Pat. Nos. 4,731,229; 5,073,236; 5,266,546; 5,431,890 and 5,730,843 which are incorporated by reference.

Referring now to the FIGURE a flow diagram of a process embodying the invention is shown. The olefins, propylene and butylene, are fed via flow line 101 into a distillation column reactor 10 into or below the reaction distillation zone which contains a bed 12 of suitable alkylation catalyst. Benzene is fed into the reactor via the reflux in line 109. Unreacted benzene and any small amounts of unreacted olefin are taken as overheads via flow line 102 and passed through finishing reactor 20 containing a bed 22 of alkylation catalyst and thence to a lights stripper column 30 which removes and separates any light material as overheads via flow line 105. Benzene and alkylate from the finishing reactor are taken as bottoms via flow line 104 and returned to the distillation column reactor 10 as reflux via flow line 109. Make up benzene is added via flow line 107.

The alkylate product and some unreacted benzene and olefins are taken as bottoms form the distillation column reactor 10 via flow line 112 and fed to the top of a benzene stripper 40 where the benzene and unreacted olefins are stripped out and taken back to the distillation column reactor 10 via flow line 113. In effect the two vessels 10 and 40 are essentially one distillation column with the vessel 10 being the rectification section and the vessel 40 being the stripping section.

The product is taken from the benzene stripper as bottoms via flow line 115 and impurities are withdrawn as a side stream via flow line 114. The product is fed to a cumene/secondary butyl benzene column 50 where the final product is taken as overheads via flow line 116. The bottoms from the cumene/secondary butyl benzene column 50 contains polyalkylated benzene and is removed and fed to dialkyl benzene column 60 via flow line 117. The dialkyl benzene is removed as overheads via flow line 118 and heavies are removed as bottoms via flow line 119.

The dialkyl benzene in flow line 118 is combined with fresh benzene in flow line 110 and fed to a transalkylation reactor 70 containing a bed 72 of transalkylation catalyst to convert dialkyl benzene to monoalkylated benzene. The effluent from the transalkylation reactor 70 is removed via flow line 120 and fed to the benzene stripping column where benzene is removed via flow line 113.

EXAMPLE

A 1 inch diameter reactor was filled with two beds of five feet each of beta zeolite catalyst. The reactor was configured such that there were two olefin injection points, one under each bed. The olefin feed (propylene or butylene) lines were set up so that either could go to either feed point. Fresh benzene was fed to the reactor as the entire reflux stream. The column was operated in a liquid continuous distillation. The reactor was operated first with propylene feed only to both beds and then through one bed only. Then butylene was fed to one bed only. Propylene was then added to both beds and finally both olefins were fed through both beds. The bottoms products from the combined feeds were collected and distilled in an Oldershaw column and the heavy cuts (to simulate benzene stripping) were analyzed by gas chromatography. Temperatures in the bed ranged from about 265 to 340° F. The overhead pressure was maintained at 75 psig. The analysis of the heavy Oldershaw cuts are shown below in TABLE I.

TABLE I

| component | First half sample | | | | Second Half Sample | | |
|---|---|---|---|---|---|---|---|
| | total | cut 10 | cut 9 | cut 8 | total | cut 10 | cut 9 |
| benzene | 75.23 | 0.05 | 1.80 | 44.72 | 88.96 | 1.36 | 96.84 |
| i-propylbenzene | 15.15 | 24.11 | 89.71 | 53.79 | 5.27 | 54.49 | 1.75 |
| n-propyl benzene | 0 | 0.02 | 0.02 | 0 | 0 | 0.02 | 0 |
| nbutylbenzene | 0 | 0.07 | 0.02 | 0 | 0 | 0.03 | 0 |
| s-butylbenzene | 7.30 | 61.06 | 8.44 | 1.16 | 3.78 | 41.26 | 0.08 |
| 1,3diPr.Benzene | 0.34 | 3.18 | 0 | 0 | 0.03 | 0.30 | 0 |
| 1,2diPr.Benzene | 0.01 | 0.10 | 0 | 0 | 0 | 0.05 | 0 |
| 1,4diButylBenzene | 0.09 | 0.89 | 0 | 0 | 0.01 | 0.13 | 0 |
| 1,4diPr.Benzene | 0.35 | 3.27 | 0 | 0 | 0.04 | 0.42 | 0 |
| 1,3dibutylbenzene | 0.18 | 1.74 | 0 | 0 | 0.03 | 0.30 | 0 |
| 1,3propylbutylbz | 0.18 | 1.67 | 0 | 0 | 0.03 | 0.38 | 0 |
| 1,4propylbutylbz | 024 | 2.30 | 0 | 0 | 0.06 | 0.69 | 0 |
| unknowns | 0 | 0 | 0 | 0.04 | 0.46 | 0 | 0.94 |
| unknowns1 | 0.02 | 0.01 | 0.02 | 0.13 | 0.08 | 0.41 | 0.36 |
| Heavies | 0.73 | 1.44 | 0 | 0 | 0 | 0.16 | 0 |
| Bromine No. | 0.51 | 0.50 | 0.42 | 0.83 | NA | NA | NA |

The invention claimed is:

1. A process for the concurrent production of cumene and secondary butyl benzene comprising the steps of:
   (a) feeding a first stream consisting essentially of benzene and a second stream consisting essentially of propylene and butylene to a distillation column reactor containing a bed of alkylation catalyst;
   (b) concurrently in said distillation column reactor;
      (i) reacting a portion of said benzene with a portion of said propylene and said butylene to form a reaction mixture containing unreacted benzene, unreacted propylene, unreacted butylene, cumene and secondary butyl benzene;
      (ii) separating the unreacted benzene, unreacted propylene and unreacted butylene from the cumene and secondary butyl benzene by fractional distillation;
   (c) removing the unreacted benzene, unreacted propylene and unreacted butylene from said distillation column reactor as overheads; and
   (d) removing the cumene and secondary butyl benzene from said distillation column reactor as bottoms.

2. The process according to claim 1 wherein there is a molar excess of benzene to propylene and butylene.

3. The process according to claim 1 wherein said overheads are fed to a finishing reactor containing a bed of alkylation catalyst to react any remaining propylene and butylene with benzene to form additional cumene and secondary butyl benzene.

4. The process according to claim 3 wherein the effluent from said finishing reactor is returned to said distillation column reactor as reflux.

5. The process according to claim 1 wherein dialkyl benzenes are formed and are removed as bottoms along with said cumene and said secondary butyl benzene and further comprising the steps of:
   (e) feeding said bottoms to a distillation column where said cumene and said secondary butyl benzene are removed as overheads and said dialkyl benzenes are removed as a second bottoms; and
   (f) feeding said second bottoms containing said dialkyl benzenes and benzene to a transalkylation reactor containing a transalkylation catalyst where a portion of said dialkyl benzene is converted to mono alkyl benzene.

6. The process according to claim 1 wherein said alkylation catalysts are selected from the group consisting of acid cation exchange resins and zeolites.

7. The process according to claim 6 wherein said alkylation catalysts comprise beta zeolite.

* * * * *